(12) United States Patent
Faram

(10) Patent No.: US 9,151,425 B2
(45) Date of Patent: Oct. 6, 2015

(54) MULTIPLE CONDUIT CONNECTOR APPARATUS AND METHOD

(75) Inventor: Joseph Dee Faram, Dallas, TX (US)

(73) Assignee: Comedica Incorporated, Dallas, TX (US)

( * ) Notice: Subject to any disclaimer, the term of this patent is extended or adjusted under 35 U.S.C. 154(b) by 459 days.

(21) Appl. No.: 12/908,909

(22) Filed: Oct. 21, 2010

(65) Prior Publication Data

US 2011/0100364 A1 May 5, 2011

Related U.S. Application Data

(60) Provisional application No. 61/257,365, filed on Nov. 2, 2009.

(51) Int. Cl.
| | |
|---|---|
| *F16L 37/60* | (2006.01) |
| *A61M 16/00* | (2006.01) |
| *A61M 16/08* | (2006.01) |
| *F16L 37/113* | (2006.01) |
| *F16L 37/56* | (2006.01) |
| *A61M 16/12* | (2006.01) |
| *A61M 11/06* | (2006.01) |

(52) U.S. Cl.
CPC ............ *F16L 37/60* (2013.01); *A61M 16/0096* (2013.01); *A61M 16/0816* (2013.01); *A61M 16/0858* (2014.02); *A61M 16/122* (2014.02); *F16L 37/113* (2013.01); *F16L 37/56* (2013.01); *A61M 11/06* (2013.01); *A61M 2016/0027* (2013.01)

(58) Field of Classification Search
CPC ....... F16L 37/60; F16L 37/133; F16L 37/565; F16L 37/56; F16L 37/50; F16L 39/00; F16L 39/005; F16L 39/02; F16L 39/04; F16L 39/06; F16L 41/03

USPC ............ 285/124.1–124.5, 325, 401, 402, 307
See application file for complete search history.

(56) References Cited

U.S. PATENT DOCUMENTS

| | | | |
|---|---|---|---|
| 402,779 | A | 5/1889 | Steinhoff |
| 1,150,238 | A | 8/1915 | Winbray |
| 2,475,468 | A * | 7/1949 | Andrews .................... 285/123.3 |

(Continued)

FOREIGN PATENT DOCUMENTS

| | | |
|---|---|---|
| EP | 1 159 918 A1 | 5/2001 |
| WO | 2007/101516 A1 | 9/2007 |
| WO | 2007/101525 A1 | 9/2007 |

OTHER PUBLICATIONS

European search report from EP 10 18 9305 dated Feb. 28, 2011, 5 pages.

*Primary Examiner* — Daniel P Stodola
*Assistant Examiner* — James Linford
(74) *Attorney, Agent, or Firm* — Hitchcock Evert LLP

(57) ABSTRACT

A multiple-conduit connector includes a first coupling part that includes multiple first connectors associated with a corresponding conduit and a second coupling part that includes multiple second connectors associated with a corresponding conduit. Each conduit of the second coupling part communicates with a corresponding conduit of the first coupling part when the first coupling part and the second coupling part are detachably connected together. The multiple-conduit connector includes a guide projection located on one coupling part and a guide recess to receive the guide projection and disposed at a corresponding location in the other coupling part.

20 Claims, 5 Drawing Sheets

(56) References Cited

U.S. PATENT DOCUMENTS

| | | | |
|---|---|---|---|
| 2,510,125 | A * | 6/1950 | Meakin .................... 174/47 |
| 2,788,991 | A * | 4/1957 | Neuhauser ................. 285/18 |
| 2,837,749 | A * | 6/1958 | Gross ....................... 4/515 |
| 3,083,707 | A | 4/1963 | Seeler |
| 3,291,122 | A | 12/1966 | Engstrom et al. |
| 3,301,255 | A | 1/1967 | Thompson |
| 3,469,863 | A * | 9/1969 | Riester et al. ............. 285/124.4 |
| 3,537,448 | A | 11/1970 | Liston |
| 3,561,444 | A | 2/1971 | Boucher |
| 3,584,621 | A | 6/1971 | Bird |
| 3,861,386 | A | 1/1975 | Harris et al. |
| 4,054,134 | A | 10/1977 | Kritzer |
| 4,062,358 | A | 12/1977 | Kritzer |
| 4,182,599 | A | 1/1980 | Eyrick et al. |
| 4,245,633 | A | 1/1981 | Erceg |
| 4,436,090 | A | 3/1984 | Darling |
| 4,558,710 | A | 12/1985 | Eichler |
| 4,601,465 | A | 7/1986 | Roy |
| 4,635,857 | A | 1/1987 | Hughes |
| 4,703,957 | A * | 11/1987 | Blenkush ................. 285/239 |
| 4,770,164 | A | 9/1988 | Lach et al. |
| 4,951,659 | A | 8/1990 | Weiler et al. |
| 4,964,404 | A | 10/1990 | Stone |
| 4,973,047 | A | 11/1990 | Norell |
| 4,981,295 | A | 1/1991 | Belman et al. |
| 5,018,517 | A | 5/1991 | Liardet |
| 5,027,809 | A | 7/1991 | Robinson |
| 5,067,707 | A | 11/1991 | Køhnke |
| 5,069,449 | A | 12/1991 | Wardwell |
| 5,107,830 | A | 4/1992 | Younes |
| 5,127,400 | A | 7/1992 | DeVries et al. |
| 5,150,291 | A | 9/1992 | Cummings et al. |
| 5,193,529 | A | 3/1993 | Labaere |
| 5,261,394 | A | 11/1993 | Mulligan et al. |
| 5,277,175 | A | 1/1994 | Riggs et al. |
| 5,322,057 | A | 6/1994 | Raabe et al. |
| 5,355,873 | A | 10/1994 | Del Bon et al. |
| 5,390,665 | A | 2/1995 | Leach |
| 5,398,676 | A | 3/1995 | Press et al. |
| 5,413,110 | A | 5/1995 | Cummings et al. |
| 5,423,313 | A | 6/1995 | Olsson et al. |
| 5,439,430 | A | 8/1995 | Rubens et al. |
| 5,451,190 | A | 9/1995 | Liardet |
| 5,535,738 | A | 7/1996 | Estes et al. |
| 5,542,416 | A | 8/1996 | Chalvignac |
| 5,547,440 | A | 8/1996 | Rubens et al. |
| 5,570,682 | A | 11/1996 | Johnson |
| 5,598,839 | A | 2/1997 | Niles et al. |
| 5,613,945 | A * | 3/1997 | Cai et al. ................. 604/288.02 |
| 5,617,847 | A | 4/1997 | Howe |
| 5,664,562 | A | 9/1997 | Bourdon |
| 5,666,945 | A | 9/1997 | Davenport |
| 5,713,349 | A | 2/1998 | Keaney |
| 5,823,179 | A | 10/1998 | Grychowski et al. |
| 5,829,429 | A | 11/1998 | Hughes |
| 5,906,198 | A | 5/1999 | Flickinger |
| 5,937,857 | A | 8/1999 | Caterini et al. |
| 5,938,117 | A | 8/1999 | Ivri |
| 5,950,619 | A | 9/1999 | Van Der Linden et al. |
| 5,964,223 | A | 10/1999 | Baran |
| 5,970,974 | A | 10/1999 | Van Der Linden et al. |
| 6,044,841 | A | 4/2000 | Verdun et al. |
| 6,058,932 | A | 5/2000 | Hughes |
| 6,076,519 | A | 6/2000 | Johnson |
| 6,076,520 | A | 6/2000 | Cooper |
| 6,079,413 | A | 6/2000 | Baran |
| 6,085,740 | A | 7/2000 | Ivri et al. |
| 6,085,746 | A | 7/2000 | Fox |
| 6,116,233 | A | 9/2000 | Denyer et al. |
| 6,152,134 | A | 11/2000 | Webber et al. |
| 6,167,881 | B1 | 1/2001 | Hughes |
| 6,170,882 | B1 * | 1/2001 | Prest ....................... 285/12 |
| 6,210,345 | B1 | 4/2001 | Van Brunt |
| 6,234,167 | B1 | 5/2001 | Cox et al. |
| 6,240,919 | B1 | 6/2001 | MacDonald et al. |
| 6,289,892 | B1 | 9/2001 | Faithfull et al. |
| 6,302,105 | B1 | 10/2001 | Wickham et al. |
| 6,336,455 | B1 | 1/2002 | Howlett |
| 6,340,025 | B1 | 1/2002 | Van Brunt |
| 6,355,002 | B1 | 3/2002 | Faram et al. |
| 6,363,932 | B1 | 4/2002 | Forchione et al. |
| 6,402,046 | B1 | 6/2002 | Loser |
| 6,405,934 | B1 | 6/2002 | Hess et al. |
| 6,412,481 | B1 | 7/2002 | Bienvenu et al. |
| 6,415,791 | B1 | 7/2002 | Van Brunt |
| 6,425,393 | B1 | 7/2002 | Lurie et al. |
| 6,427,690 | B1 | 8/2002 | McCombs et al. |
| 6,450,163 | B1 | 9/2002 | Blacker et al. |
| 6,467,476 | B1 | 10/2002 | Ivri et al. |
| 6,526,976 | B1 | 3/2003 | Baran |
| 6,540,153 | B1 | 4/2003 | Ivri |
| 6,540,154 | B1 | 4/2003 | Ivri et al. |
| 6,546,927 | B2 | 4/2003 | Litherland et al. |
| 6,550,472 | B2 | 4/2003 | Litherland et al. |
| 6,550,476 | B1 | 4/2003 | Ryder |
| 6,557,549 | B2 | 5/2003 | Schmidt et al. |
| 6,568,387 | B2 | 5/2003 | Davenport et al. |
| 6,571,790 | B1 | 6/2003 | Weinstein |
| 6,581,596 | B1 | 6/2003 | Truitt et al. |
| 6,581,598 | B1 | 6/2003 | Foran et al. |
| 6,581,600 | B2 | 6/2003 | Bird |
| 6,588,421 | B1 | 7/2003 | Diehl et al. |
| 6,588,422 | B1 | 7/2003 | Berthon-Jones et al. |
| 6,595,203 | B1 | 7/2003 | Bird |
| 6,598,602 | B1 | 7/2003 | Sjoholm |
| 6,598,603 | B1 | 7/2003 | Andersson et al. |
| 6,609,517 | B1 | 8/2003 | Estes et al. |
| 6,612,303 | B1 | 9/2003 | Grychowski et al. |
| 6,615,831 | B1 | 9/2003 | Tuitt et al. |
| 6,626,175 | B2 | 9/2003 | Jafari et al. |
| 6,631,721 | B1 | 10/2003 | Salter et al. |
| 6,640,806 | B2 | 11/2003 | Yurko |
| 6,644,304 | B2 | 11/2003 | Grychowski et al. |
| 6,644,310 | B1 | 11/2003 | Delache et al. |
| 6,644,311 | B1 | 11/2003 | Truitt et al. |
| 6,663,574 | B2 | 12/2003 | Faram et al. |
| 6,679,258 | B1 | 1/2004 | Strom |
| 6,694,969 | B1 | 2/2004 | Heinonen et al. |
| 6,702,998 | B2 | 3/2004 | Conner |
| 6,708,688 | B1 | 3/2004 | Rubin et al. |
| 6,718,969 | B1 | 4/2004 | Rubin et al. |
| 6,722,362 | B2 | 4/2004 | Hete et al. |
| 6,729,334 | B1 | 5/2004 | Baran |
| 6,737,042 | B2 | 5/2004 | Rabinowitz et al. |
| 6,752,151 | B2 | 6/2004 | Hill |
| 6,776,159 | B2 | 8/2004 | Pelerossi et al. |
| 6,799,605 | B1 * | 10/2004 | Van Scyoc et al. ...... 137/614.03 |
| 6,805,120 | B1 | 10/2004 | Jeffrey et al. |
| 6,823,866 | B2 | 11/2004 | Jafari et al. |
| 6,848,443 | B2 | 2/2005 | Schmidt et al. |
| 6,851,425 | B2 | 2/2005 | Paul et al. |
| 6,854,462 | B2 | 2/2005 | Berthon-Jones et al. |
| 6,904,906 | B2 | 6/2005 | Salter et al. |
| 6,907,881 | B2 | 6/2005 | Suki et al. |
| 6,910,479 | B1 | 6/2005 | Van Brunt |
| 6,915,803 | B2 | 7/2005 | Berthon-Jones et al. |
| 6,932,084 | B2 | 8/2005 | Estes et al. |
| 6,948,497 | B2 | 9/2005 | Zdrojkowski et al. |
| 6,968,840 | B2 | 11/2005 | Smith et al. |
| 7,011,091 | B2 | 3/2006 | Hill et al. |
| 7,036,500 | B2 | 5/2006 | Niles et al. |
| 7,059,324 | B2 | 6/2006 | Pelerossi et al. |
| 7,066,176 | B2 | 6/2006 | Jaffe et al. |
| 7,070,761 | B2 | 7/2006 | Rabinowitz et al. |
| 7,100,607 | B2 | 9/2006 | Zdrojkowski et al. |
| 7,128,069 | B2 | 10/2006 | Farrugia et al. |
| 7,165,547 | B2 | 1/2007 | Truitt et al. |
| 7,188,621 | B2 | 3/2007 | DeVries et al. |
| 7,191,776 | B2 | 3/2007 | Niles et al. |
| 7,191,780 | B2 | 3/2007 | Faram |
| 7,204,245 | B2 | 4/2007 | Johnson et al. |
| 7,210,480 | B2 | 5/2007 | Lurie et a |
| 7,232,417 | B2 | 6/2007 | Plante |
| 7,302,949 | B2 | 12/2007 | Pelerossi et al. |

(56) References Cited

U.S. PATENT DOCUMENTS

| | | |
|---|---|---|
| 7,445,607 B2 | 11/2008 | Plante |
| 7,469,700 B2 | 12/2008 | Baran |
| 7,472,702 B2 | 1/2009 | Beck et al. |
| 7,472,705 B2 | 1/2009 | Baran |
| 7,500,481 B2 | 3/2009 | Delache et al. |
| 7,562,657 B2 | 7/2009 | Blanch et al. |
| 7,600,511 B2 | 10/2009 | Power et al. |
| 7,699,054 B2 | 4/2010 | Pelerossi et al. |
| 2001/0004893 A1 | 6/2001 | Biondi et al. |
| 2002/0020412 A1 | 2/2002 | Gilbert et al. |
| 2002/0163194 A1* | 11/2002 | Mintz et al. ............ 285/361 |
| 2003/0051731 A1 | 3/2003 | Be'eri et al. |
| 2003/0140925 A1 | 7/2003 | Sapienza et al. |
| 2003/0205229 A1 | 11/2003 | Crockford et al. |
| 2005/0061318 A1 | 3/2005 | Faram |
| 2005/0109340 A1 | 5/2005 | Tehrani |
| 2005/0165334 A1 | 7/2005 | Lurie |
| 2005/0212286 A1* | 9/2005 | Smith, III ............... 285/124.1 |
| 2005/0217666 A1 | 10/2005 | Fink et al. |
| 2006/0084877 A1 | 4/2006 | Ujhazy et al. |
| 2006/0144398 A1 | 7/2006 | Doshi et al. |
| 2006/0178245 A1 | 8/2006 | Schiller et al. |
| 2006/0201500 A1 | 9/2006 | Von Hollen et al. |
| 2006/0243274 A1 | 11/2006 | Lieberman et al. |
| 2006/0272642 A1 | 12/2006 | Chalvignac |
| 2007/0017522 A1 | 1/2007 | Be-Eri et al. |
| 2007/0017523 A1 | 1/2007 | Be-Eri et al. |
| 2007/0089740 A1 | 4/2007 | Baumert et al. |
| 2007/0186928 A1 | 8/2007 | Be-Eri |
| 2008/0000475 A1 | 1/2008 | Hill |
| 2008/0000477 A1 | 1/2008 | Huster et al. |
| 2008/0015456 A1 | 1/2008 | McCawley et al. |
| 2008/0091117 A1 | 4/2008 | Choncholas et al. |
| 2008/0190429 A1 | 8/2008 | Tatarek |
| 2008/0283060 A1 | 11/2008 | Bassin |
| 2009/0020121 A1 | 1/2009 | Bassin |

* cited by examiner

MULTIPLE CONDUIT CONNECTOR APPARATUS AND METHOD

CROSS-REFERENCE TO RELATED APPLICATIONS

The present application claims the benefit, under 35 U.S.C. §119(e), of U.S. Provisional Application No. 61/257,365 which was filed Nov. 2, 2009 and which is hereby incorporated by reference herein.

BACKGROUND

The present disclosure relates to a multiple conduit connector that may be used for simultaneously interconnecting multiple tubes. More particularly, the present disclosure relates to a multiple conduit connector including a quick action lock/release mechanism having a self-alignment feature enhancing proper interconnection for each of the individual tubes.

Many applications involve numerous tubes or hoses for conveying gases, liquids, and the like. For example, in robotics numerous tubes or hoses are sometimes needed to provide the desired control and operation of the multiplicity of movements involved. In many hospitals and medical offices in which numerous tools are used, there is a need for a multiplicity of tubes carrying the various control and operating gases or liquids to each of the individual tools or patient interfaces. Regardless of the application, it is oftentimes very desirable to be able to simultaneously disconnect or connect a multiplicity of the individual tubes.

As a result of this need, multiple tube connectors have been developed. Multiple tube connectors typically employ at least two coupling parts having paths for the flow of gas or liquid therethrough which are suitably connected to the ends of the tubing and then interconnected to one another so as to provide gas or liquid communication between the two sets of tubing. Oftentimes, one of the coupling parts is mounted on a panel.

There are several problems noted with current multiple tube connectors. For example, many multiple tube connectors have a threaded fastener to connect the two coupling parts. Threaded fasteners sometimes require a substantial amount of time to be threaded to connect multiple tube connectors. Furthermore, threaded fasteners that are threaded at an incorrect angle may become cross-threaded and damaged. Additionally, threaded fasteners may be connected incorrectly, such that the two coupling parts connect the wrong tubes to each other. Moreover, if an appropriate substantially gas-tight or liquid-tight seal is desired between the coupling parts, the threaded fasteners need to be properly tightened.

Depending on the person tightening the fasteners and/or the tools available, the degree to which the coupling parts are tightened may vary substantially. In addition, individual tubing inserts may be threaded into threaded apertures of the coupling parts and may then individually inserted into the ends of their respective tubing. Further, a seal may be provided for each of the threaded inserts, which may also result in a varying degree of tightness. Furthermore, oftentimes the seals may not be self-retaining and may be easily lost. From the above discussion, it is clear that some prior art multiple tube connectors may be difficult and cumbersome to use. Another drawback is that multiple tube connectors are often made from two dissimilar pieces, which may result in increased manufacturing cost.

SUMMARY

The present invention comprises an apparatus or method that has any one or more of the features listed in the appended claims and/or any one or more of the following features, which alone or in any combination may comprise patentable subject matter:

Multiple conduit connectors according to the present disclosure solve the above-described and other problems associated with current multiple tube connectors. Rather than being referred to as a multiple tube connector, the present disclosure provides a multiple conduit connector because the coupling parts of the present disclosure actually connect multiple conduits, with the multiple conduits indirectly connecting multiple tubes in the illustrative embodiments.

In some contemplated embodiments, the coupling parts connect multiple tubes on one side of the multiple conduit connector with a special type of adapter on the other side of the coupling parts. One of the pair of coupling parts includes a guide projection while the other of the pair includes a guide recess. When the guide projection is inserted in the guide recess as the pair of coupling parts are brought closer together, the insertion facilitates the proper alignment of the corresponding conduits on each of the coupling parts. Therefore, the coupling parts may be connected together quickly without concerns about accidentally aligning the conduits on one coupling part with non-corresponding conduits on the other coupling part. Such a connection may be accomplished in an amount of time that is much shorter than the amount of time typically required for using a threaded fastener to connect the two coupling parts.

According to the present disclosure, a securing mechanism or means to reduce the possibility of accidental disengagement of the coupling parts without requiring the lengthy time for threading a fastener is provided. The securing mechanism may require only a quick and simple rotation of a coupling part to lock the coupling parts securely together. Furthermore, the multiple conduit connector may be manufactured inexpensively from plastic, with the components of one of the coupling parts manufactured easily and inexpensively as an integrally formed single unit. Apparatuses according to the present disclosure may be used for rapidly connecting multiple medical tubes that are used for a breathing treatment, for example, and in a manner that ensures that each tube is connected properly and securely.

Therefore, the present disclosure provides a method for connecting multiple tubes which is quicker than threading fasteners. According to this disclosure, a multiple conduit connector secures multiple tubes using secured seals that maintain appropriate gas-tight or liquid tight connections. A multiple conduit connector according to the present disclosure secures multiple tubes to prevent accidental disengagement. Multiple conduit connectors according to the present disclosure allow for connections made by different operators to be secured to a substantially identical extent, such that the individual manual dexterity of an operator has less influence on the effectiveness of the connection.

Multiple conduit connectors contemplated herein are also cost effective in their manufacture and do not significantly increase the time required to train operators in their use. In some applications, multiple conduit connectors of the present disclosure allow for efficient and sanitary connections of patient interfaces for treating respiratory conditions.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
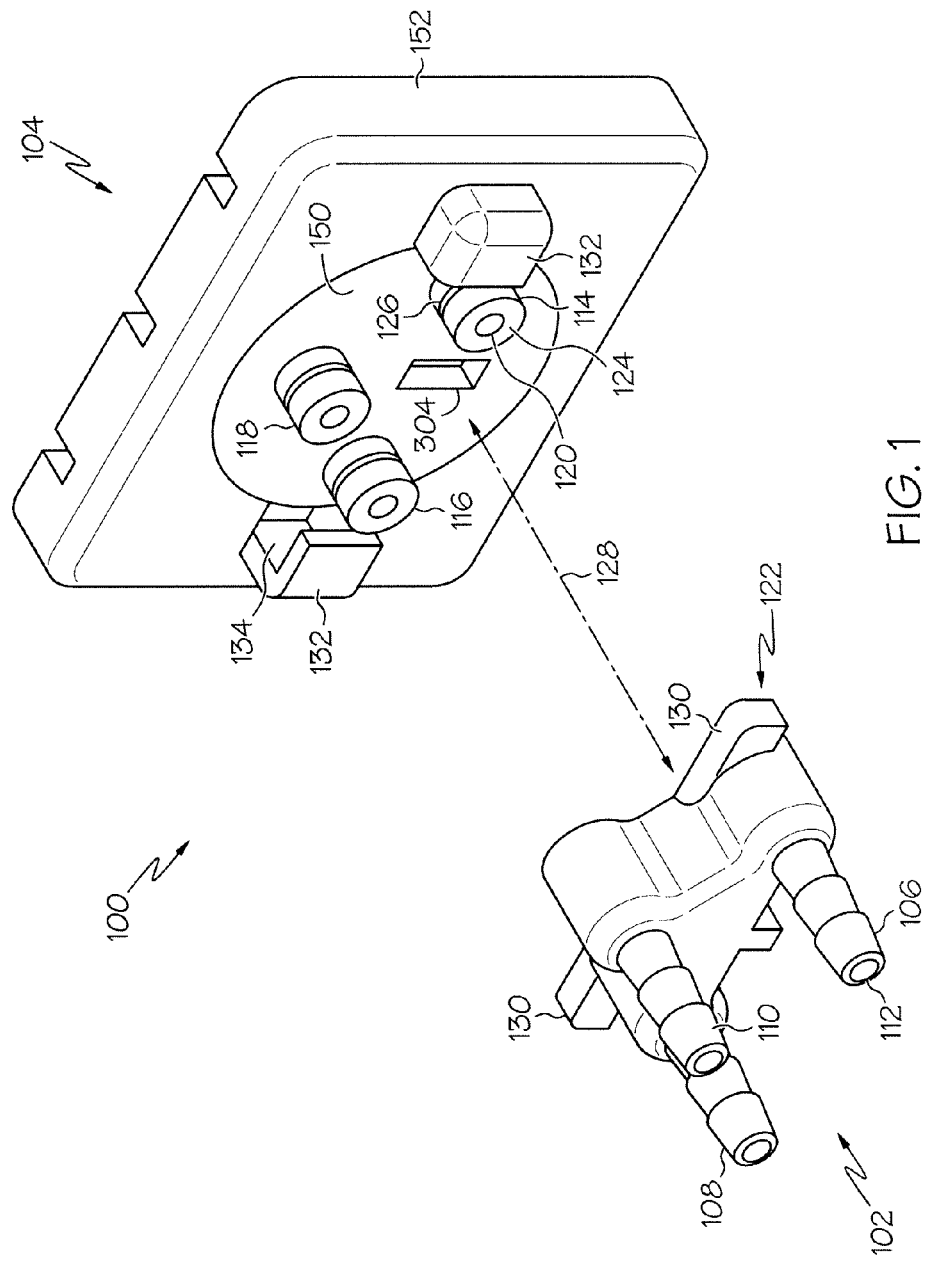
FIG. 1 is a perspective view of a first coupling part and a second coupling part according to the present disclosure.

FIG. 1 is a view of a multiple conduit connector 100, which includes a first coupling part 102 and a second coupling part 104. The first coupling part 102 includes multiple connectors, such as first connectors 106, 108, 110. Although FIG. 1 depicts the first coupling part 102 with three first connectors 106, 108, 110, the first coupling part 102 may have two or more of these connectors. Each of the first connectors 106, 108, 110 includes a corresponding conduit. For example, the first connector 106 includes a corresponding conduit 112. If a tube or hose is attached to the end of any of the first connectors 106, 108, 110, the corresponding conduit enables a gas or liquid that may pass through the tube or hose to also pass through the attached connector.

The second coupling part 104 includes multiple second connectors, such as a second connector 114, a second connector 116, and a second connector 118. Although FIG. 1 depicts the second coupling part 104 with three second connectors 114, 116, 118, the second coupling part 104 may have two or more of these connectors. Each of the second connectors 114, 116, 118 includes a corresponding conduit. For example, the second connector 114 includes a corresponding conduit 120. If a tube or hose is attached to the end of any of the second connectors 114, 116, 118, the corresponding conduit enables a gas or liquid that may pass through the tube or hose to also pass through the attached connector.

The second connectors 114, 116, 118 pair with the first connectors 106, 108, 110. Each conduit of the second coupling part 104 is associated with a corresponding conduit of the first coupling part 102 when the first connectors 106, 108, 110 of the first coupling part 102 are connected with the second connectors 114, 116, 118 of the second coupling part 104. For example, the conduit 120 of the second connector 114 is aligned with the conduit 112 of the first connector 106 when the first coupling part 102 and the second coupling part 104 are connected together. One end of each of the second connectors 114, 116, 118 pairs with a corresponding end of one of the first connectors 106, 108, 110 when the first coupling part 102 and the second coupling part 104 are placed together. For example, one end 122 of the first connector 106 is paired with one end 124 of the second connector 114 when the first coupling part 102 is connected to the second coupling part 104. In this manner, each conduit and each connector of the first coupling part 102 is aligned with and connected to a corresponding conduit and a corresponding connector of the second coupling part 104. This alignment and connection of multiple conduits is why the apparatus of FIG. 1 is referred to as the multiple conduit connector 100.

The first coupling part 102 may be an integrally formed single unit. For example, if the first coupling part 102 is an integrally formed single unit manufactured from a plastic material, a metal, and/or a synthetic resin, the second coupling unit 104 may be manufactured from the same plastic material, metal, and/or synthetic resin. Manufacturing both coupling parts 102 and 104 from the same material may be less expensive than manufacturing both coupling parts 102 and 104 from different materials. Likewise, manufacturing each conduit and each connector of the first coupling part 102 as a single integral unit may be less expensive than manufacturing each component of the first coupling part 102 separately and then assembling the separately manufactured components.

Each of the first connectors 106, 108, 110 may include a corresponding resilient sealing ring for providing a substantially gas tight seal and/or a substantially liquid tight seal between each of the corresponding first connectors 106, 108, 110 and the corresponding second connectors 114, 116 118. Alternatively or additionally, each of the second connectors 114, 116, 118 may include a corresponding resilient sealing ring for providing a seal between each of the corresponding first connectors 106, 108, 110 and the corresponding second connectors 114, 116, 118. For example, the second connector 114 includes a resilient sealing ring 126 that provides a substantially gas tight seal between the second connector 114 and the corresponding first connector 106. The resilient sealing ring 126 may be a self-retaining and replaceable "O" ring made of a high fluorine fluoroelastomer. A self-retaining "O" ring reduces many of the prior art problems with retaining proper seals. Connecting the first coupling part 102 and the second coupling part 104 together may result in radial compression of the resilient sealing ring 126 between the first connector 106 and the second connector 114. The radial compression may result in creating a substantially gas-tight or liquid-tight seal.

The first coupling part 102 and the second coupling part 104 may be connected together by a simple movement, such as a movement of the first coupling part 102 along the path 128. Securing means may secure the first coupling part 102 to the second coupling part 104 when the first coupling part 102 and the second coupling part 104 are connected together by the simple movement. The securing means may lock the first coupling part 102 and the second coupling part 104 together when the first coupling part 102 and/or the second coupling part 104 is rotated to a locked position. When the first coupling part 102 and the second coupling part 104 are connected and secured, corresponding first connectors 106, 108, 110 and second connectors 114, 116, 118 are interconnected so as to provide corresponding substantially sealed flow paths through the first coupling part 102 and the second coupling part 104. The securing means also allows for separation of the first coupling part 102 and second coupling part 104 when the first coupling part 102 and/or the second coupling part 104 are rotated to a released position.

FIG. 1 depicts the securing means described in the following example, but other types of securing means may be implemented as known by those of skill in the art. In FIG. 1, the securing means includes a pair of first members 130 extending radially outwardly from the first coupling part 102 in opposite directions and a pair of second members 132 extending perpendicularly from the second coupling part 104. Alternatively, the first members 130 may extend longitudinally from the first coupling part 102 and the second members 132 may extend radially outwardly from the second coupling part 104. Each second member 132 includes a slot 134 that is perpendicular to the longitudinal orientation of the second member 132 as shown in FIG. 1 (only one slot 134 is visible in FIG. 1). The first members 130 are received in slots 134 of the second members 134 when the first coupling part 102 is rotated relative to the second coupling member 104, such as counter-clockwise rotation.

The second members 132 engage the first members 130, acting as a stop for limiting axial rotation beyond the second member 132, such as limiting counter-clockwise rotation, when the first members 130 are received inside the slots 134. Receipt of the first members 130 in the slots 134 of the second members 132 prevents the first coupling part 102 and the second coupling part 104 from accidental disengagement. Engagement through the rotation of the coupling parts 102, 104 to secure the first member 130 in the slot 134 of the second member 132 may be much quicker than using threaded fasteners to secure the coupling parts 102 and 104 together.

In at least one embodiment, at least one of the first connectors 106, 108, 110 is longitudinally-extending and at least two of the first connectors 106, 108, 110 may be parallel to each other. Alternatively, at least one of the second connectors 114, 116, 118 is longitudinally-extending and at least two of the second connectors 114, 116, 118 may be parallel to each other. For example, FIG. 1 depicts each of the second connectors 114, 116, 118 as longitudinally-extending from the second coupling part 104 and parallel to each of the other second connectors 114, 116, 118. At least one of the second connectors 114, 116, 118 may be a male connector and at least one of the first connectors 106, 108, 110 may be a female connector. For example, FIG. 1 depicts each of the second connectors 114, 116, 118 as a male connector and each of the corresponding first connectors 106, 108, 110 as a female connector.

Figure 2:
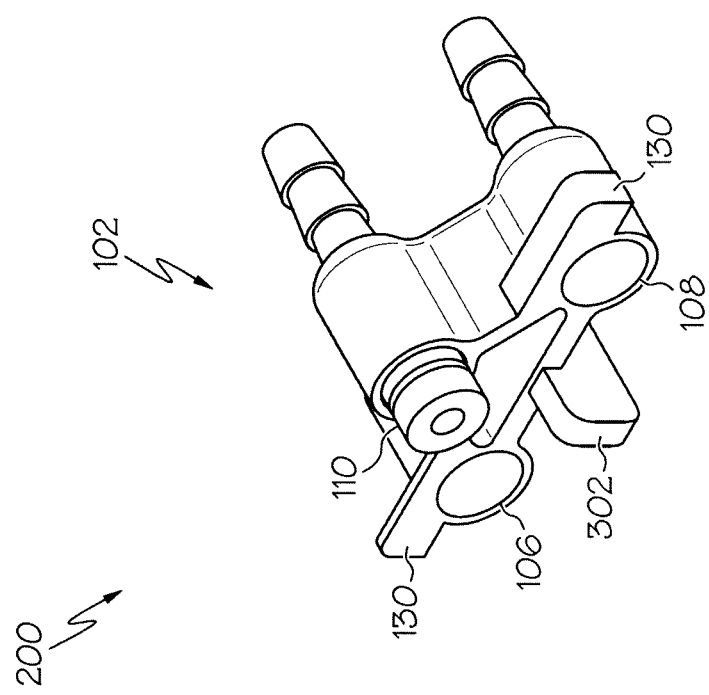
FIG. 2 is another perspective view of another first coupling part according to the present disclosure.

FIG. 2 depicts another view 200 of another first coupling part 102. At least one of the second connectors 114, 116, 118 may be a female connector and at least one of the first connectors 106, 108, 110 may be a male connector. For example, FIG. 2 depicts that the first connectors 106 and 108 may be female connectors that correspond to the second connectors 114 and 116 which are male connectors, while the first connector 110 is a male connector that corresponds to the second connector 118 which may be a female connector in the FIG. 2 example. In this manner, the second connectors 114, 116, 118 may be any combination of male connectors and female connectors provided that the corresponding first connectors 106, 108, 110 provide the corresponding female connectors and male connectors, respectively.

Figure 3:
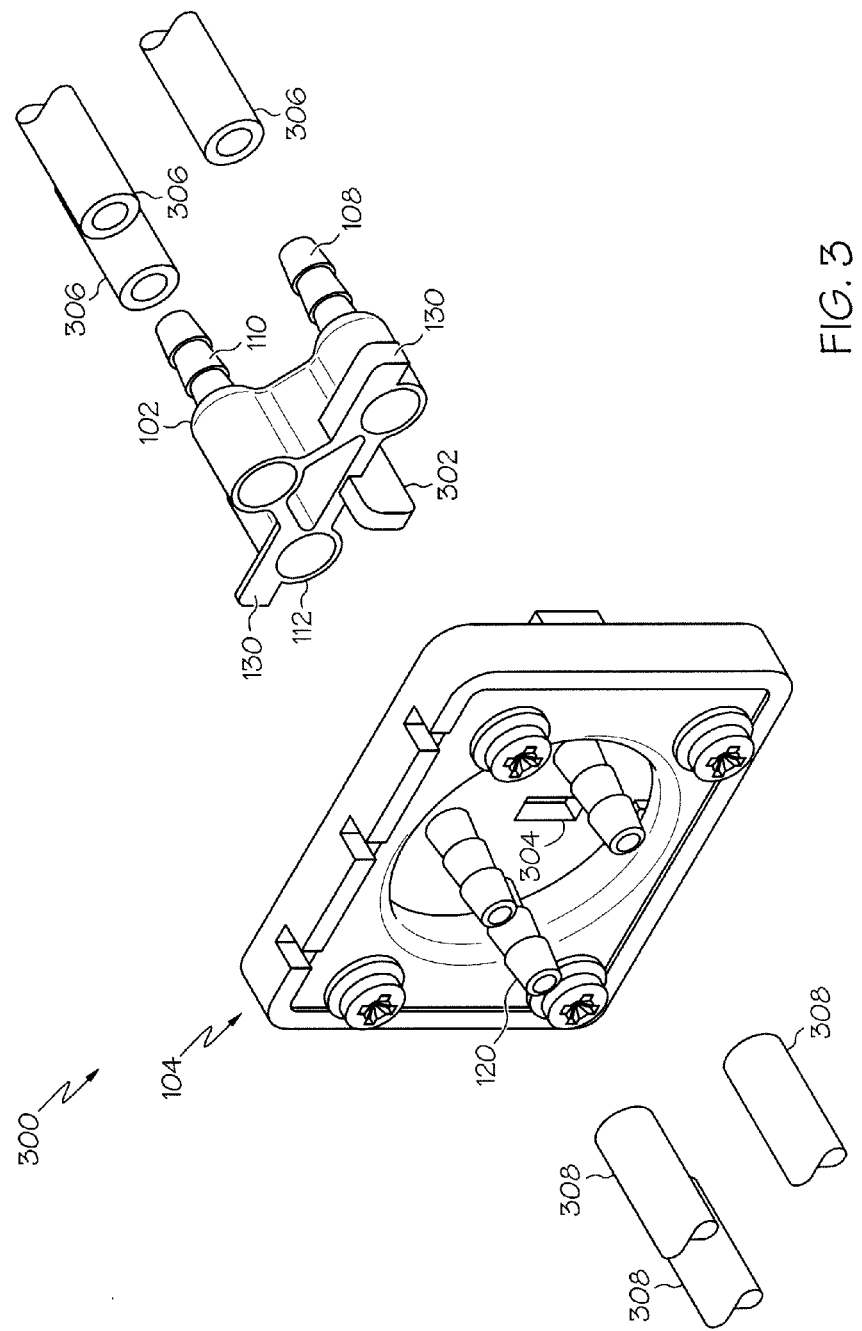
FIG. 3 is another perspective view of the first coupling part and the second coupling part according to the present disclosure.

FIG. 3 depicts another view 300 of the first coupling part 102 and the second coupling part 104. A guide projection 302 may be located on the first coupling part 102. Alternatively, the guide projection 302 may be located on the second coupling part 104. In the embodiment depicted in FIG. 3, the second coupling part 104 includes a guide recess 304 to receive the guide projection 302. Alternatively, the guide recess 304 may be at a corresponding location in the first coupling part 102. If the guide projection 302 is off-centrally disposed, then the guide recess 304 is correspondingly off-centrally disposed, as depicted in FIG. 3.

The guide projection 302 may be longitudinally extended further than either the first connectors 106, 108, 110 are longitudinally extended from the first coupling part 102 or the second connectors 114, 116, 118 are longitudinally extended from the second coupling part 104. By extending longitudinally further than the connectors 106, 108, 110 and 114, 116, 118, the guide projection 302 may engage the guide recess 304 before any of the first connectors 106, 108, 110 engage any of the second connectors 114, 116, 118. The guide projection 302 may be formed in a specific shape and the guide recess 304 may correspond to the specific shape, whereas a guide projection for a different multiple conduit connector may be formed in a different shape and the guide recess for the different multiple conduit connector may correspond to the different shape. Due to the difference in shapes of the guide projections, insertion of any guide projection may not be possible in the wrong guide recess. Such a feature may be beneficial at a location that utilizes various different multiple conduit connectors.

Insertion of the guide projection 302 in the guide recess 304 ensures proper alignment of each conduit and each connector of the second coupling part 104 with a corresponding conduit and connector of the first coupling part 102. For example, the conduit 112 for the first connector 106 is aligned with the corresponding conduit 120 for the second connector 114 when the guide projection 302 is inserted in the guide recess 304. Aligning conduits with corresponding conduits is particularly important when each conduit communicates a different type of gas or liquid, such that improper alignment of conduits may result in conduits communicating the wrong type of gas or liquid to a port of a medical device or a patient interface. Additionally or alternatively, the securing means may include the guide projection 302 when located and rotated in the guide recess 304. For example, the guide projection 302 may serve as a key that is inserted into the guide recess 304 and rotated in the guide recess 304. After such a rotation, a portion of the guide projection 302 and/or a portion of the guide recess 304 prevent removal of the guide projection 302 until the guide projection 302 is rotated back to its original insertion orientation. Furthermore, one of the connectors 106, 108, 110 may serve as the guide projection if it is a male connector that extends further longitudinally than any of the other male connectors extend longitudinally.

In some embodiments, such as the illustrative embodiment of FIG. 1, connectors 106, 108, 110 are integrally molded with a disk 150 that is rotatable relative to a main body 152 of coupling part 104. In FIG. 1, disk 150 is shown in an orientation having guide recess 304 at a six o'clock position relative to main body 154. However, coupling part 102 cannot couple to coupling part 104 when disk 150 is in this six o'clock orientation because first member 130 will engage outer walls of second members 132. Thus, prior to connecting coupling part 102 to coupling part 104, disk 150 is rotated clockwise until guide recess 304 is at roughly a seven or eight o'clock orientation. Coupling part 102 is then coupled to coupling part 104 with connectors 114, 116, 118 being received in the conduits associated with connectors 106, 108, 110 and with guide projection 302 being received in guide recess 304. However, at this point in the coupling process, first members 130 of coupling part 102 are outside slots 134 but project beyond the periphery of disk 150 in close proximity to main body 152. Disk 150, along with coupling part 102, are then rotated counter-clockwise relative main body 152 of coupling part 104 to move member 130 into the slots 134 of members 132 thereby to complete the coupling process.

The multiple conduit connector 100 may include a first set of tubes 306. Each of the first set of tubes 306 may be secured to the first connectors 106, 108, 110 to form a set of extensions corresponding to each corresponding conduit of the first coupling part 102. The multiple conduit connector 100 may also include a second set of tubes 308. Each of the second set of tubes 308 may be secured to the second connectors 114, 116, 118 to form a set of extensions corresponding to each corresponding conduit of the second coupling part 104.

The first connectors 106, 108, 110 may be permanently or removably secured to each of the first set of tubes 306 and/or the second connectors 114, 116, 118 may be permanently secured to each of the second set of tubes 308. Each of the connectors 106, 108, 110 and 114, 116, 118 may be configured to enhance securement of one of either the first set of tubes 306 or the second set of tubes 308. For example, each corresponding connector may be sized and shaped to frictionally receive a portion of one of the first set of tubes 306 or one of the second set of tubes 308. Frictionally receiving a portion of one of the tubes may involve a force-fit. At least one tube of the first set of tubes 306 and/or the second set of tubes 308 may be manufactured from a molded or extruded polymeric material selected from the group consisting of polyolefins, polyesters, polyamides, polyimides, polysulfones, polycarbonates, fluoro-polymers, silicone polymers, polyurethanes, polyalkyleneterephthalates, and combinations thereof.

At least one of the first set of tubes 306 or the second set of tubes 308 may be connected to a patient interface, such as a breathing head assembly for a continuous high-frequency oscillation breathing treatment apparatus. The first set of tubes 306 or the second set of tubes 308 may include a gas tube connected to a pulsating gas input of the breathing head assembly and/or a nebulizer tube connected to a nebulizer of the breathing head assembly. Another tube of the first set of tubes 306 or the second set of tubes 308 may be a monitoring tube connected to a pressure monitoring port of the breathing head assembly. Either the first coupling part 102 or the second coupling part 104 may be secured to a source of breathable gas to form a set of extensions corresponding to each corresponding conduit and connector. A control for the source of breathable gas may enable an operator to provide a patient with a continuous high-frequency oscillation breathing treatment and to discontinue providing the patient with the continuous high-frequency oscillation breathing treatment. However, the second set of tubes 308 may not be required in the event that the second coupling part 104 is to be permanently connected to the breathable gas source, or if breathable gas source is fitted with a special type of adapter which is capable of interfacing with the connectors of the second coupling part 104 in such a way as to create a substantially gas tight connection between the breathable gas source and the second coupling part 104.

Figure 4:
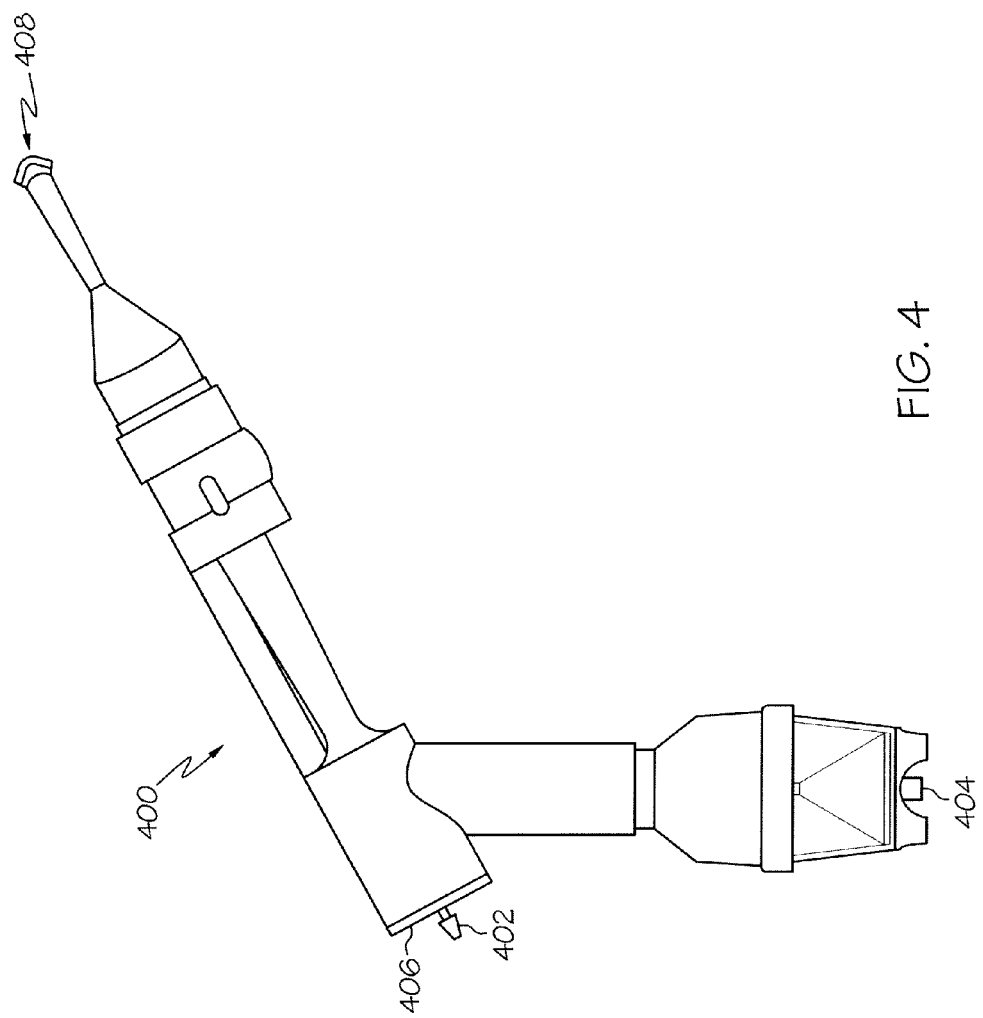
FIG. 4 is a side elevation view of a patient interface according to the present disclosure.

FIG. 4 is a view of a patient interface 400 according to the present disclosure. The patient interface 400 may be a breathing head assembly for a continuous high-frequency oscillation breathing treatment apparatus. Examples of a breathing head assembly and a breathing treatment apparatus may be seen in U.S. Pat. No. 7,191,780 which is titled "Continuous High-Frequency Oscillation Breathing Treatment Apparatus;" U.S. Patent Application Publication No. 2007/0256690 A1 which is titled "Breathing Treatment Apparatus," and U.S. Patent Application Publication No. 2008/0066754 A1 which is titled "Continuous High-Frequency Oscillation Breathing Treatment Apparatus," each of the foregoing of which is hereby expressly incorporated by reference herein.

The patient interface 400 may include a pulsating gas input 402 and a nebulizer 404, each of which may be connected to the first set of tubes 306. Nebulizer technology is well known in the art and does not need to be recounted here. Examples of nebulizer technology may be seen at U.S. Pat. No. 6,929,003, Nebulizer Apparatus and Method, and U.S. Pat. No. 6,748,945, Nebulizer Apparatus and Method. While the disclosed embodiment describes the patient interface 400 as including the nebulizer 404, it should be apparent to one skilled in the art that the nebulizer 404 is not required for all applications and that the present disclosure contemplates embodiments in which the nebulizer 404 is excluded. The patient interface 400 may also include a pressure monitoring port 406 which may also be connected to the first set of tubes 306. As a patient exhales back into a mouthpiece 408 of the patient interface 400, some of the exhalation gas exits the pressure monitoring port 406. In a preferred embodiment, proximal pressure is transmitted from a patient back through a pressure sensing tube which is connected to the pressure monitoring port 406. Pressure can be monitored by connecting a manometer (not shown) to the pressure monitoring port 406.

The patient interface 400 may enable treating a variety of breathing disorders experienced by patients. The patient interface 400 is particularly suited to the treatment of atelectasis, the partial or total collapse of the lung, although those skilled in the art will appreciate that it has applications in treating other disorders as well. In a patient suffering from atelectasis, the lung can become partially or completely deflated due to fluid buildup, or from physical pressure such as from a trauma or tumor. If this occurs, the lung may not be able to re-inflate on its own, which can in turn exacerbate the patient's condition leading to a progressively worsening physical state or even death. Treating a patient with atelectasis traditionally has required the use of multiple types of apparatus connected by multiple tubes to a breathable gas source in order to provide the multiple types of treatment used. The present disclosure provides for a multiple conduit connector that enables quickly providing multiple types of treatment, depending on the needs of the patient.

In some embodiments, to begin a breathing therapy session, the clinician selects one of one or more breathing treatment modes depending on the condition of the patient. For example, the clinician may select between a lung expansion CPEP™ mode (Continuous Positive Expiratory Pressure) or a secretion mobilization CHFO™ mode (Continuous High-frequency Oscillation) although those skilled in the art will recognize that alternative therapies could be selected without deviating from the scope and content of the present disclosure. After the therapy has been initiated, the patient may begin the therapy by placing his or her mouth onto the mouthpiece 408 of the patient interface 400 and begin breathing normally.

If CPEP™ mode has been chosen, the gas flow is linear. IF CHFO™ mode has been chosen, gas flow is pulsatile in nature at a substantially constant amplitude. In some contemplated embodiments, gas flow is regulated or adjusted so that it is pulsitile at a rate of from 1 to 15 hertz at substantially constant amplitude. Following the desired amount of time in therapy, the use of the patient interface 400 may be discontinued. In an alternative embodiment, the breathing head assembly 400 may be equipped with a nebulizer dryer spray nozzle.

Figure 5:
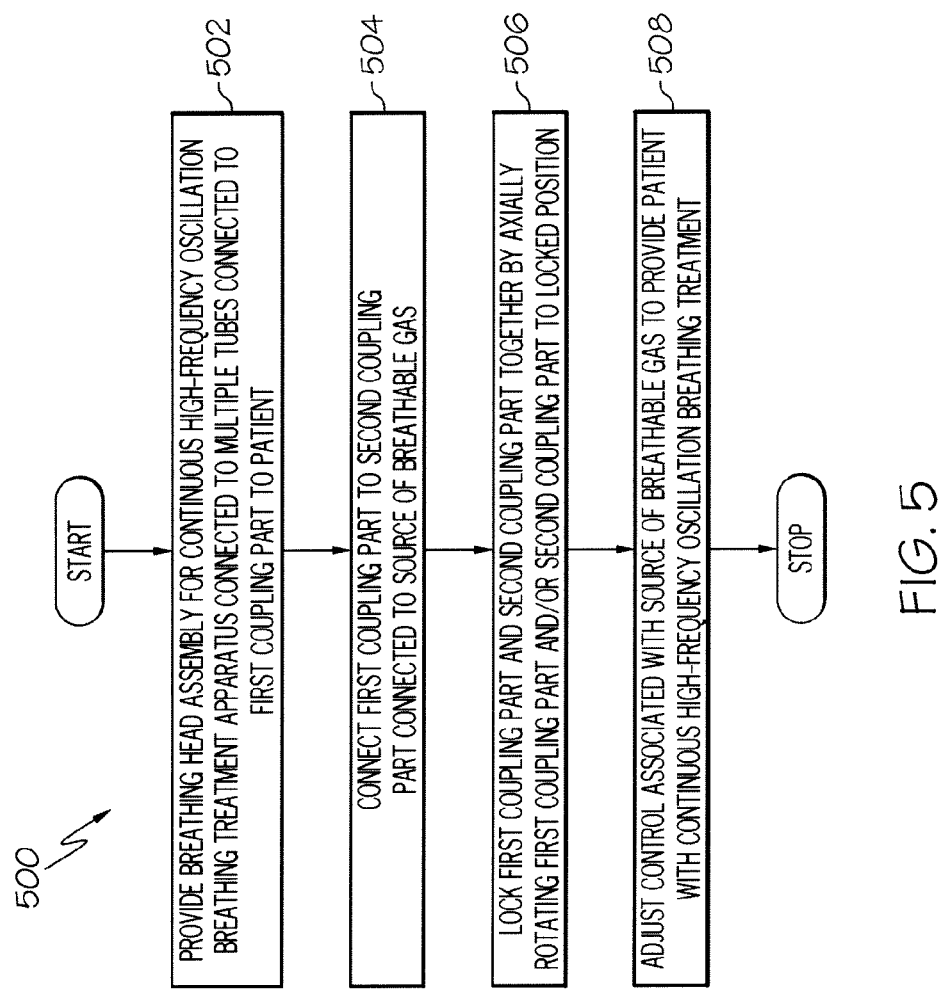
FIG. 5 is a flowchart of a method of the present disclosure.

FIG. 5 depicts a flowchart of a method 500 according to the present disclosure. Executing the method 500 may enable an operator to provide a patient with a continuous high-frequency oscillation breathing treatment. In box 502, a breathing head assembly for a continuous high-frequency oscillation breathing treatment apparatus connected to multiple tubes connected to a first coupling part is provided to a patient. For example, the patient interface 400 connected to the first set of tubes 306 connected to the first coupling part 102 is provided to a patient.

In box 504, a first coupling part is connected to a second coupling part connected to a source of breathable gas. For example, an operator connects the first coupling part 102 to the second coupling part 104, which is connected to source of breathable gas. In box 506, a first coupling part and a second coupling part are locked together by axially rotating the first coupling part and/or the second coupling part to a locked position. For example, the operator locks the first coupling part 102 and the second coupling part 104 together by rotating the first coupling part 102 counter-clockwise to a locked position as discussed above.

In box 508, a control associated with a source of breathable gas is adjusted to provide a patient with a continuous high-frequency oscillation breathing treatment. For example, the operator adjusts the control for the source of breathable gas to provide the patient with continuous high-frequency oscillation breathing treatment. When the operator decides that the breathing treatment is completed, the operator may adjust the same control to discontinue providing the patient with the continuous high-frequency oscillation breathing treatment, rotate the first coupling part 102 clockwise to a release position to unlock the first coupling part 102 from the second coupling part 104, and disconnect the first coupling part 102 from the second coupling part 104.

Additional embodiments according to the present disclosure are also possible. In another embodiment, the described continuous high-frequency oscillation breathing treatment apparatus can be connected to, and be incorporated into, a ventilator circuit. In some embodiments, the continuous high-frequency oscillation breathing treatment apparatus includes a means for supplying its own compressed gas rather than relying on an external gas source. Such means could include means for receiving and/or storing containers of compressed gas, or onboard compressor means for creating compressed gas. In some embodiments, the patient interface is disposable.

In the illustrated embodiment, the first coupling part 102 includes the trio of first connectors 106, 108, 110 arranged in a generally triangular pattern. Each of the trio of first connectors 106, 108, 110 is a female connector that includes a corresponding conduit, such as conduit 112. Each of the trio of first connectors 106, 108, 110 is between 0.25 and 0.75 inches in length, such as 0.51 inches, with a conduit that has a diameter of between 0.075 and 0.225 inches, such as 0.144 inches. The first coupling part 102, the trio of first connectors 106, 108, 110, and each corresponding conduit are an integrally formed single unit manufactured from a plastic material, a metal, and/or a synthetic resin.

In the illustrated embodiment, the second coupling part 104 includes a trio of second connectors 114, 116, 118 arranged in a generally triangular pattern to pair with the trio of first connectors 106, 108, 110. Each of the trio of second connectors 114, 116, 118 is a longitudinally-extending and parallel male connector that includes a corresponding conduit, such as conduit 120. Each conduit, such as conduit 120, of the second coupling part 104 is associated with a corresponding conduit, such as conduit 112, of the first coupling part 102 when the first coupling part 102 and the second coupling part 104 are detachably connected together by an axial movement. An end, such as the end 124, of each of the trio of second connectors 114, 116, 118 is adapted to pair with a corresponding end, such as the end 122, of one of the trio of first connectors 106, 108, 110 when the first coupling part 102 and the second coupling part 104 are placed in an abutting relationship. The second coupling part 104 is manufactured from a plastic material, a metal, and/or a synthetic resin.

Further in the illustrated embodiment, each of the trio of second connectors 114, 116, 118 includes a corresponding resilient sealing ring for providing a substantially gas tight seal and/or a substantially liquid tight seal between a corresponding one of the trio of first connectors 106, 108, 110 and the trio of second connectors 114, 116, 118. The corresponding resilient sealing ring is a self-retaining and replaceable "O" ring made of a high fluorine fluoroelastomer in some embodiments. Engaging the first coupling part 102 and the second coupling part 104 promotes radial compression of the resilient sealing ring between the trio of first connectors 106, 108, 110 and the trio of second connectors 114, 116, 118.

In the illustrated embodiment, the guide projection 302 is located on the first coupling part 102, and is between 0.125 and 0.375 inches long, such as 0.25 inches, and between 0.125 and 0.375 inches high, such as 0.248 inches. The guide projection 302 is off-centrally disposed and is longitudinally extended further than the trio of second connectors 114, 116, 118 is longitudinally extended.

In the illustrated embodiment, the guide recess 304 is between 0.125 and 0.375 inches high, such as 0.248 inches high, disposed at a corresponding location in the second coupling part 304, and is correspondingly off-centrally disposed to receive the guide projection 302. Insertion of the guide projection 302 in the guide recess 304 promotes alignment of each conduit of the second coupling part 104 with each corresponding conduit of the first coupling part 102.

Further in the illustrated embodiment, securing means secures the first coupling part 102 to the second coupling part 104 by locking the first coupling part 102 and the second coupling part 104 together when the first coupling part 102 and/or the second coupling part 104 is axially rotated to a locked position. When locked, corresponding ones of the trio of first connectors 106, 108, 110 and the trio of second connectors 114, 116, 118 are securely interconnected so as to provide a corresponding trio of flow paths through the first coupling part 102 and the second coupling part 104. The securing means allows for separation of the first coupling part 102 and the second coupling part 104 when the first coupling part 104 and/or the second coupling part 104 is axially rotated to a release position. The securing means includes the pair of first members 130 extending radially outward from the first coupling part 102 and the pair of second members 132 extending longitudinally from the second coupling part 104. The second members 132 each include a slot 134 disposed perpendicular to the longitudinal orientation of the second member 132. The slots 134 receive the first members 130 when the first coupling part 102 is axially rotated relative to the second coupling member 104. Portions of the second members 132 act as a stop for limiting axial rotation of the first members 130 such that first members 130 are not able to rotate past second members 132.

Also in the illustrated embodiment, each of the first trio of tubes 306 is secured to the first coupling part 102 to form a trio of extensions corresponding to each corresponding conduit of the first coupling part 102. Each corresponding connector 106, 108, 110 is configured to enhance securement of, frictionally receive, or force fit, one of the first trio of tubes 306 to the first coupling part 102. The first trio of tubes 306 is manufactured from a molded or extruded polymeric material selected from the group consisting of polyolefins, polyesters, polyamides, polyimides, polysulfones, polycarbonates, fluoro-polymers, silicone polymers, polyurethanes, polyalkyleneterephthalates, and combinations thereof.

The first trio of tubes 306 is connected to a patient interface such as the breathing head assembly 400 for a continuous high-frequency oscillation breathing treatment apparatus. The first trio of tubes 306 includes a gas tube connected to the pulsating gas input 402 of the breathing head assembly 400, a nebulizer tube connected to the nebulizer 404 of the breathing head assembly 400, and a monitoring tube connected to the pressure monitoring port 406 of the breathing head assembly 400.

Further in the illustrated embodiment, each of the second trio of tubes 308 is secured to the second coupling part 104 to form a trio of extensions corresponding to each corresponding conduit of the second coupling part 104. Each corresponding connector 114, 116, 118 is configured to enhance securement of, frictionally receive, or force fit, one of the second trio of tubes 308 to the second coupling part 104. The second trio of tubes 308 is manufactured from a molded or extruded polymeric material selected from the group consisting of polyolefins, polyesters, polyamides, polyimides, polysulfones, polycarbonates, fluoro-polymers, silicone polymers, polyurethanes, polyalkyleneterephthalates, and combinations thereof. The second coupling part 104 is secured to a source of breathable gas to form a trio of extensions corresponding to each corresponding conduit, such as conduit 120, of the second coupling part 104.

Although certain illustrative embodiments have been described in detail above, many embodiments, variations and modifications are possible that are still within the scope and spirit of this disclosure as described herein and as defined in the following claims.

The invention claimed is:

1. A multiple-conduit connector comprising:
    a first coupling part comprising a plurality of first connectors, wherein each of said plurality of first connectors comprises a corresponding conduit passage;
    a second coupling part comprising a main body and a disk that is rotatable relative to said main body, wherein said disk comprises a plurality of second connectors to pair with said plurality of first connectors, wherein each of said plurality of second connectors comprises a corresponding conduit passage, wherein each conduit passage of said second coupling part is associated with a corresponding conduit passage of said first coupling part when said first coupling part and said second coupling part are detachably connected together;
    a guide projection located on a primary one of said first coupling part and said disk at a position separate from any conduit passage;
    a guide recess to receive said guide projection and disposed at a corresponding location in a secondary one of said first coupling part and second coupling part, wherein insertion of said guide projection in said guide recess promotes alignment of said each conduit passage of said second coupling part with said corresponding conduit passage of said first coupling part, the guide projection being a fixed member;
    a securing means which locks said first coupling part together with said second coupling part when said first coupling part including said plurality of first connectors and said disk including said plurality of second connectors are axially rotated relative to said main body in a first direction about an axis parallel with the plurality of first and second connectors, wherein corresponding ones of said plurality of first connectors and said plurality of second connectors are interconnected so as to provide a corresponding plurality of flow paths through said first coupling part and said second coupling part, and said securing means allows for separation of said first coupling part and said second coupling part when said first coupling part including said plurality of first connectors and said disk including said plurality of second connectors are axially rotated in a second direction about the axis,
    wherein said securing means comprises a first member extending radially outward from one of said first coupling part and said main body, and a second member extending longitudinally from one of said first coupling part and said main body, wherein said second member comprises a slot disposed perpendicular to the longitudinal orientation of said second member, wherein said slot receives said first member when said first coupling part is axially rotated relative to said main body in the first direction.

2. The multiple-conduit connector of claim 1, wherein said first coupling part comprises said plurality of first connectors and said guide projection as an integrally formed single unit.

3. The multiple-conduit connector of claim 1, wherein said second coupling part comprises said plurality of second connector and said guide projection as an integrally formed single unit.

4. The multiple-conduit connector of claim 1, wherein at least one of said plurality of first connectors is a male connector and at least one of said plurality of second connectors is a female connector.

5. The multiple-conduit connector of claim 1, wherein said at least one of plurality of first connectors is a female connector and at least one of said plurality of second connectors is a male connector.

6. The multiple-conduit connector of claim 1, wherein at least one of said plurality of first connectors and at least one of said plurality of second connectors is longitudinally-extending and substantially parallel with each other.

7. The multiple-conduit connector of claim 1, wherein an end of each of said plurality of second connectors is adapted to pair with a corresponding end of one of said plurality of first connectors when said first coupling part and said second coupling part are placed in an abutting relationship.

8. The multiple-conduit connector of claim 1, wherein said guide projection is longitudinally extended further than either said plurality of first connectors is longitudinally extended and said plurality of second connectors is longitudinally extended.

9. The multiple-conduit connector of claim 1, wherein said guide projection is off-centrally disposed, and wherein said guide recess is correspondingly off-centrally disposed.

10. The multiple-conduit connector of claim 1, wherein said guide projection is formed in a specific shape, and wherein said guide recess is formed to correspond to said specific shape.

11. The multiple-conduit connector of claim 1, wherein at least one of said plurality of first connectors and said plurality of second connectors further comprises a corresponding resilient sealing ring for providing at least one of a substantially gas tight seal and a substantially liquid tight seal between a corresponding one of said plurality of first connectors and a corresponding one of said plurality of second connectors.

12. The multiple-conduit connector of claim 11, wherein said corresponding resilient sealing ring is a self-retaining and replaceable "0" ring made of a high fluorine fluoroelastomer.

13. The multiple-conduit connector of claim 11, wherein engaging said first coupling part and said second coupling part promotes radial compression of said resilient sealing ring between said plurality of first connectors and said plurality of second connectors.

14. The multiple-conduit connector of claim 1, wherein said first coupling part comprises said first member and said main body comprises said second member.

15. A multiple-conduit connector comprising:
    a first coupling part comprising:
        a plurality of first connectors, wherein each of said plurality of first connectors comprises a corresponding conduit passage,
        a fixed guide projection at a position separate from any conduit passage, and a first member extending from said first coupling part in a direction radially outward from an axis parallel with the plurality of first connectors; and a second coupling part comprising:

a disk comprising a plurality of second connectors to pair with said plurality of first connectors, wherein each of said plurality of second connectors comprises a corresponding conduit passage, wherein each conduit of said second coupling part is associated with a corresponding conduit passage of said first coupling part when said first coupling part and said second coupling part are detachably connected together, and a guide recess to receive said guide projection disposed at a corresponding location in said second coupling part, wherein insertion of said guide projection in said guide recess promotes alignment of said each conduit passage of said second coupling part with said corresponding conduit passage of said first coupling part, and a main body comprising a second member extending longitudinally from said main body which comprises a slot disposed perpendicular to the longitudinal orientation of said second member, wherein said slot is dimensioned to receive said first member, wherein said disk is rotatable relative to said main body;

wherein said first coupling part and said second coupling part are secured together when said first coupling part including said plurality of first connectors and said disk including said plurality of second connectors are axially rotated in a first direction about said axis causing said first member to engage said slot of said second member, wherein corresponding ones of said plurality of first connectors and said plurality of second connectors are interconnected so as to provide a corresponding plurality of flow paths through said first coupling part and said second coupling part when secured together; and wherein said first coupling part and said second coupling part are separable when said first coupling part including said plurality of first connectors and said disk including said plurality of second connectors are axially rotated in a second direction about the axis.

16. The multiple-conduit connector of claim 15, wherein at least one of said plurality of first connectors is a male connector and at least one of said plurality of second connectors is a female connector.

17. The multiple-conduit connector of claim 15, wherein said at least one of plurality of first connectors is a female connector and at least one of said plurality of second connectors is a male connector.

18. The multiple-conduit connector of claim 15, wherein said guide projection is longitudinally extended further than either said plurality of first connectors is longitudinally extended and said plurality of second connectors is longitudinally extended.

19. The multiple-conduit connector of claim 15, wherein said guide projection is off-centrally disposed, and wherein said guide recess is correspondingly off-centrally disposed.

20. The multiple-conduit connector of claim 15, wherein at least one of said plurality of first connectors and said plurality of second connectors further comprises a corresponding resilient sealing ring for providing at least one of a substantially gas tight seal and a substantially liquid tight seal between a corresponding one of said plurality of first connectors and a corresponding one of said plurality of second connectors.

* * * * *

UNITED STATES PATENT AND TRADEMARK OFFICE
CERTIFICATE OF CORRECTION

PATENT NO.         : 9,151,425 B2                                    Page 1 of 1
APPLICATION NO.    : 12/908909
DATED              : October 6, 2015
INVENTOR(S)        : Joseph Dee Faram It is certified that error appears in the above-identified patent and that said Letters Patent is hereby corrected as shown below:

In the specification

Column 1, line 46: delete "gas-tight" and insert --gas tight--

Column 1, line 47: delete "liquid-tight" and insert --liquid tight--

Column 1, line 53: insert --be-- between "then" and "individually"

Column 2, line 48: delete "gas-tight" and insert --gas tight--

Column 4, line 35: delete "gas-tight" and insert --gas tight--

Column 4, line 36: delete "liquid-tight" and insert --liquid tight--

Column 5, line 3: delete "134" and insert --132--

Column 6, line 56: insert --first-- between "move" and "member"

Column 6, line 57: insert --second-- between "of" and "members"

Column 8, lines 23-24: delete "appa-ratus" and insert --appa-ratuses--

Column 8, line 42: delete "IF" and insert --If--

Column 8, line 65: insert --a-- between "to" and "source"

In the claims

Column 12, line 51: delete "'0' ring" and insert --'O' ring--

Signed and Sealed this
Fifth Day of April, 2016

Michelle K. Lee
*Director of the United States Patent and Trademark Office*